United States Patent [19]

May et al.

[11] 4,415,591
[45] Nov. 15, 1983

[54] USE OF AMINOALKYL PHENYL SULFIDE DERIVATIVES FOR THE TREATMENT OF HYPERTENSION

[75] Inventors: Sheldon W. May, Atlanta, Ga.; Robert S. Phillips, Gaithersburg, Md.; Heath H. Herman, Chamblee; Patricia W. Mueller, Decatur, both of Ga.

[73] Assignee: Georgia Tech Research Institute, Atlanta, Ga.

[21] Appl. No.: 270,247

[22] Filed: Jun. 4, 1981

[51] Int. Cl.$^3$ .............................................. A61K 31/10
[52] U.S. Cl. ................................... 424/330; 564/341
[58] Field of Search ........................ 424/330; 564/341

[56] References Cited

U.S. PATENT DOCUMENTS

| | | | |
|---|---|---|---|
| 3,318,953 | 5/1967 | Wehrmeister | 548/239 |
| 3,519,686 | 7/1970 | Nair et al. | 424/330 |
| 3,908,007 | 9/1975 | Util et al. | 424/242 |
| 3,911,015 | 10/1975 | Andrisano | 424/330 |
| 3,991,198 | 11/1976 | Fuxe | 424/267 |
| 4,065,584 | 12/1977 | Lafon | 424/244 |
| 4,134,918 | 1/1979 | Bey et al. | 424/320 |
| 4,134,996 | 1/1979 | Dunbar et al. | 424/319 |
| 4,199,597 | 4/1980 | Neustadt et al. | 424/309 |
| 4,260,634 | 4/1981 | Wehrmeister | 424/330 |

OTHER PUBLICATIONS

May et al., J.A.C.S. 102, 5981–5984, 1980.

*Primary Examiner*—Jane T. Fan
*Attorney, Agent, or Firm*—Newton, Hopkins & Ormsby

[57] ABSTRACT

Hypertension in mammals can be treated by administering an effective amount of an aminoalkyl phenyl sulfide having the formula

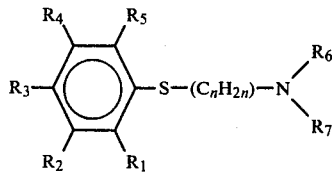

wherein
 $(C_nH_{2n})$ = a linear or branched alkyl chain of 10 carbons or less (n = 1–10);
 $R_1, R_2, R_3, R_4, R_5$, = H, OH, $C_1$–$C_4$-alkyl, $C_1$–$C_4$-alkoxy, F, Cl, Br, or I;
 $R_6$ $R_7$ = H, $C_1$–$C_4$-alkyl;

and the pharmaceutically acceptable salts thereof. The hypotensive potential of the compounds may be evaluated by oxygenation with dopamine-beta-hydroxylase.

8 Claims, No Drawings

USE OF AMINOALKYL PHENYL SULFIDE DERIVATIVES FOR THE TREATMENT OF HYPERTENSION

BACKGROUND OF THE INVENTION

1. Field of the Invention

This invention relates to a method for treating hypertension by the administration of aminoalkyl phenyl sulfide derivatives. Moreover, it relates to a method for evaluating the effectiveness of these compounds through oxygenation by dopamine-beta-hydroxylase.

2. Description of the Prior Art

Logical approaches to the treatment of hypertension require an understanding of the biochemistry and enzymology of the body as it relates to the problems of high blood pressure. Prior art discloses the presence of compounds containing phenyl sulfides and amino groups biologically active as anti-microbial agents, anti-depressives, appetite suppressants, anti-hypertensives and anti-inflammatory agents.

Wehrmeister U.S. Pat. No. 3,318,953 and U.S. Pat. No. 4,260,634 discloses a method of synthesis of phenylthioalkylamines and amides thereof together with their use as anti-fungal and anti-bacterial agents in metalworking oil or chemical lubricants. No disclosure relating to a pharmacological use is made.

Nair et al. U.S. Pat. No. 3,519,686 discloses 1-(4-chlorophenyl)-mercapto-2-propylamine and salts thereof for use as an anti-depressive or mood elevator. However, these compounds are not disclosed as antihypertensive agents for use in lowering blood pressure.

Andrisano, U.S. Pat. No. 3,911,015, discloses the use of alkanol-thio-alkylamines and their salts as therapeutic agents useful in treating peripheral vasodilatory and hypertensive problems. Andrisano discloses compounds containing 2 aromatic rings connected by an alkyl chain containing a thio and a nitro group. This compound is clearly distinguishable from the aminoalkyl phenyl sulfide derivatives of the present invention in that the two aromatic groups are required as well as the presence of an alkyl group connecting the nitrogen to the phenol group.

Lafon, U.S. Pat. No. 4,065,584 discloses anorexigenic agents (appetite suprressants) and analgesic or anti-inflammatory properties of sulphur-containing arylamine derivatives. These compounds all include a nitrogen-containing saturated heterocyclic ring. Therefore, the compounds and utilities disclosed by Lafon are different from those of the present invention.

Neustadt, U.S. Pat. No. 4,199,597 discloses polyfluoro substituted phenoxy and phenylthio alkanoic acids having antihypertensive activity. These compounds are structurally different from those of the present invention in that a polyfluoro-containing group is present on the aromatic ring.

The prior art fails to disclose a unifying approach to hypertensive treatment as is found in the present invention. The prior art does not disclose the use of the aminoalkyl phenyl sulfide derivatives of the present invention as antihypertensive agents. In a broader sense the present invention contains the insight of evaluating a compound as a substrate for dopamine-beta-hydroxylase. This use of a purified enzyme system to oxygenate the sulfur group reflects a strategy of analysis which permits evaluation of both the enzymatic parameters and products formed by dopamine-beta-hydroxylase when acting on the compound of interest. This permits the design of therapeutic strategies involving the specific aminoalkyl phenyl sulfides disclosed and enzymes that modify them such as the dopamine-beta-hydroxylase and monoamine oxidase. Therefore, this invention also satisfies a need for a fast and effective method of evaluating the disclosed hypotensive compounds in vitro and allows a more precise method for developing effective treatment of hypertension.

SUMMARY OF THE INVENTION

Accordingly, it is an object of this invention to provide a novel method for treating hypertension in mammals.

A further object is to provide a method for treating hypertension in mammals by administration of aminoalkyl phenyl sulfide derivatives.

A further object is to evaluate the potential therapeutic value of specific aminoalkyl sulfide derivatives.

A further object is to provide a method for evaluating potential substrate analogs of catecholamine and monoamine metabolism.

Further objects of the invention will become apparent from the disclosure which follows.

These objects have been attained by a process for treating hypertension in mammals comprising administering to a mammal an effective amount of an aminoalkyl phenyl sulfide derivative having the formula

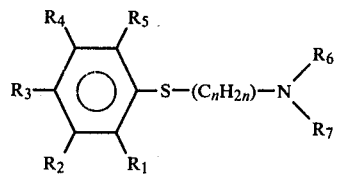

wherein:
 ($C_nH_{2n}$) = a linear or branched alkyl chain having 10 carbon atoms or less (n = 1–10)
 $R_1$, $R_2$, $R_3$, $R_4$, $R_5$ = H, OH, $C_1$–$C_4$-alkoxy, $C_1$–$C_4$-alkyl, F, Cl, Br, I;
 $R_6$, $R_6$ = H, $C_1$–$C_4$-alkyl;
and pharmaceutically acceptable acid addition salts thereof.

In another embodiment the invention comprises a process for evaluating the potential therapeutic value of specific aminoalkyl phenyl sulfide derivatives by oxygenating them in aqueous solution by the action of dopamine-beta-hydroxylase, determining the catalytic constant for the oxygenation of the individual aminoalkyl phenyl sulfide derivatives and comparing the catalytic constant so obtained with the catalytic constant of standard substrates for dopamine-beta-hydroxylase in this assay.

DETAILED DESCRIPTION OF THE INVENTION AND PREFERRED EMBODIMENTS

In the compounds used in the process of this invention, the phenyl ring can be substituted or unsubstituted. Suitable substituents $R_1$–$R_5$ include $C_1$–$C_4$-alkyl groups, such as methyl, ethyl, n-propyl, isopropyl, n-butyl, isobutyl, sec-butyl, and t-butyl; $C_1$–$C_4$-alkoxy groups such as methoxy, ethoxy, n-propoxy, isopropoxy, n-butoxy, isobutoxy, sec-butoxy, t-butoxy, hydroxy, and halogen, such as fluorine, chlorine, bromine and iodine. The amino group may be substituted or unsubstituted. Suitable substituents include $C_1$–$C_4$ alkyl groups such as those enumerated above. The alkyl chain between the sulfur atom and the amino group may be any linear or branched chain divalent hydrocarbon group. Suitable groups include methylene, ethylene, 1,3-propylene 1,4-butylene, 1,6-hexylene, octamethylene, decamethylene, 2-methyl-1,3-propylene, 3-methyl-1,5-pentylene, 3-ethyl-1,5-pentylene, 2-ethyl-1,6-pentylene, 2-ethyl-1,6-hexylene, 2-ethyl-1,8-octylene, 5-methyl-1,9-nonylene, and the like.

Suitable compounds useful in the process of this invention include 2-aminoethyl phenyl sulfide, 2-(methylamino)ethyl phenyl sulfide, 2-(dimethylamino)ethyl phenyl sulfide, 2-(ethylamino)ethyl phenyl sulfide, 2-(n-propylamino)ethyl phenyl sulfide, 2-(n-butylamino)ethyl phenyl sulfide, 2-aminoethyl 4-hydroxyphenyl sulfide, 2-aminoethyl 3,4-dihydroxyphenyl sulfide, 2-aminoethyl 3,5-dihydroxyphenyl sulfide, 2-aminoethyl 4-methyl phenyl sulfide, 2-aminoethyl 2,4-dimethyl phenyl sulfide, 2-aminoethyl 4-ethyl phenyl sulfide, 2-aminoethyl 4-propylphenyl sulfide, 2-aminoethyl 4-butylphenyl sulfide, 2-aminoethyl 4-methoxyphenyl sulfide, 2-aminoethyl 4-ethoxy phenyl sulfide, 2-aminoethyl 4-propoxyphenol sulfide, 2-aminoethyl 4-butoxyphenyl sulfide, 2-aminoethyl 3,4-dimethoxyphenyl sulfide, 2-aminoethyl 3,4,5-trimethoxyphenyl sulfide, 3-aminopropyl phenyl sulfide, 4-aminobutyl phenyl sulfide, 6-aminohexyl phenyl sulfide, 8-aminooctyl phenyl sulfide, 10-aminodecyl phenyl sulfide, 6-amino-2-ethylhexyl phenyl sulfide, 3-amino-2-methylpropyl 3,4-dihydroxyphenyl sulfide, 4-amino-3-methylbutyl 3,4-dimethoxyphenyl sulfide, 4-methylamino-3-methylbutyl 3,4-dimethoxyphenyl sulfide, and the like.

The compounds used in the process of this invention are readily synthesized by methods known to those skilled in the art. For example, the procedure disclosed by Wehrmeister, U.S. Pat. Nos. 3,318,953 and 4,260,634 may be used to prepare compounds suitable for the method of treatment of this invention.

The compounds used in the process of this invention may also be used in the form of their acid addition salts with non-toxic pharmaceutically acceptable acids. Such salts include the hydrochloride, sulfate, hydrobromide, citrate, acetate, gluconate, and the like.

A preferred compound for use in the process of this invention is 2-aminoethyl phenyl sulfide.

In practicing the process of this invention the antihypertensive compounds may be administered orally, parenterally or rectally and may be formulated in compositions and dosage forms for such administration. In these compositions and dosage forms the compounds are admixed with conventional non-toxic pharmaceutical excipients. Solid dosage forms for oral administration include capsules, tablets, pills, powders, and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may be also comprise buffering agents. Tablets and pills can also be prepared with an enteric coating.

Liquid dosage forms for oral administration include pharmaceutically acceptable emulsions, solutions, suspensions, syrups, and elixirs containing inert diluents commonly used in the art, such as purified water and alcohols. Besides inert diluents, such compositions can also include adjuvants, such as wetting agents, emulsifying and suspending agents, and sweetening, flavoring, and perfuming agents. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.5 to 100 mg/kg of body weight daily are administered to mammals to obtain effective relief of hypertension. A preferred dosage level is 1.0 to 10.0 mg/kg of body weight.

In treating hypertension in mammals by the method of this invention, it is preferred to administer the aminoalkyl phenyl sulfide in combination with a monoamine oxidase inhibitor, which may have the effect of prolonging the life of the active compounds in the body.

The combination of aminoalkyl phenyl sulfide derivatives and monoamine oxidase inhibitors such as clorgyline, deprenyl, nardil (phenethylhydrazine sulfate) or others currently in clinical use may protect the sulfide or sulfoxide product and therefore allow a longer active period in the body, resulting in an increased anti-hypertensive effect.

Although the exact mechanism by which the compounds used in the process of this invention exert their physiological effect is uncertain, and applicants do not wish to be bound by any theoretical considerations, it is possible that the compounds may play the role, at least in part, of false neurotransmitters. According to Williams, "Textbook of Endocrinology," W. D. Saunders Co., 1974, p. 292, the criteria for a false neurotransmitter include the following:

(1) Generally, they are not normally present in the sympathetic neurons in significant quantities.

(2) They can be made to accumulate in the nerve endings at the same site as the natural transmitters.

(3) They must be held in the same storage sites, released by the same nerve stimulation, and depleted by drugs that deplete norepinephrine.

The compounds used in the process of this invention bear some resemblence to the catecholamines which are involved in neurotransmission in that they can act as excellent substrates for dopamine-beta-hydroxylase. Early assertions of false neurotransmitters such as aldomet ($\alpha$-methyldopamine) proved to be incorrect. ("Pharmacological Basis of Therapeutics," Ed. by L. Goodman and Alfred Gilman, 4th Ed. 1970, and 6th Ed. 1980, McMillan Co.).

The disclosed aminoalkyl phenyl sulfide derivatives or their enzymatic oxygenation products may function as false neurotransmitters. Dopamine-beta-hydroxylase [EC 1.14.2.1], a copper-containing monooxygenase present in a variety of mammalian tissues, catalyzes the conversion of dopamine to norepinephrine, thus playing a key role in the biosynthethetic conversion of potent neurotransmitters and in the production of adrenaline.

The first demonstration of sulfoxidation by dopamine-beta-hydroxylase was reported with phenyl 2-aminoethyl sulfide as substrate (S. W. May and R. S. Phillips, J. Am. Chem. Soc. 102, 5983–5984, 1980).

The effectiveness of the compounds used in the process of this invention as anti-hypertensive agents can be evaluated by such an enzymatic oxygenation process. In this process the aminoalkyl phenyl sulfide is contacted with the enzyme dopamine-beta-hydroxylase in aqueous solution in the presence of molecular oxygen, an electron donor, e.g. hexacyanoferrate (II) or ascorbate, and the necessary cofactors for the enzyme, such as a source of copper (II) ions, and at a pH range, maintained by a suitable buffer, of 3 to 8, preferably about 5 to 6, and at a temperature of 20° to 47° C., preferably about 37° C.

It is preferred to use purified enzyme, e.g. dopamine-beta-hydroxylase prepared from bovine adrenals by a modification of the method of Ljones et al., European Journal of Biochemistry 1976, 61, 525–533. It is preferred to use an enzyme having an activity of 12–15 units per milligram in the presence of fumarate and copper and hexacyanoferrate(II) or ascorbate as the electron donor. The presence of copper greatly accelerates the oxygenation of the substrate and hence it is preferred that copper (II) ion be present in the solution at a concentration of 3–5 micromolar. The oxygenation is also accelerated by the presence of fumarate. Accordingly, it is preferred that fumarate be present in the reaction mixture in a concentration of at least 10 millimolar.

The preferred concentration of hexacyanoferrate(II), when it is used as the electron donor, is about 2 millimolar. When ascorbic acid is used as an electron donor it is preferred that it be present in a concentration of about 10 millimolar. When ascorbic acid is used as the electron donor it is also preferred that about 200 micrograms per milliliter of catalase be present in the reaction mixture.

The progress of the oxygenation reaction may be followed by any convenient method. For example, when hexacyanoferrate(II) is used as the electron donor, the reaction may be followed spectrophotometrically, by measuring the optical absorbance at 420 nm; when ascorbic acid is used as the electron donor the reaction may be followed by measuring the oxygen uptake using a polarographic electrode and an oxygen monitor.

The catalytic constants for the oxygenation of each substrate are then determined by conventional procedures such as the method of Eisenthal and Cornish-Bowden, (1974) Biochem. J., 139, 715–720, or by using the computer program of Cleland to fit the hyperbolic form of the Michaelis-Menten equation (Cleland, W. W., Adv. Enzymol. Relat. Areas Mol. Biol. 1967, 29, 1–32).

In order to evaluate the potential hypotensive activity of aminoalkyl phenyl sulfides, the catalytic constants for each of the compounds are compared with the catalytic constants for standard substrates for dopamine-beta-hydroxylase such as tyramine and 2-phenylethylamine. The greater the catalytic constant of the particular substrate, the more reactive the substrate is with the enzyme dopamine-beta-hydroxylase. The more reactive the substrate is with the enzyme, the greater its potential competitive effect with the natural substrate in the body. Since dopamine-beta-hydroxylase is a major enzyme in the synthetic pathway of the catecholamines in the body, it would be expected that the presence in the body of a competitive substrate would act to decrease the amount of catecholamines produced, and thereby have an hypotensive effect.

Therefore, by a comparison of the relative values of the catalytic constants for the various aminoalkyl phenyl sulfide substrates, the compounds which have superior hypotensive activity can be selected.

Having now fully described the invention, it will be apparent to one of ordinary skill in the art that many changes and modifications may be made thereto without departing from the spirit or scope of the invention as set forth herein.

EXAMPLE 1

A reaction solution was prepared having concentrations of 5 micromolar $CuSO_4$, 10 mM sodium fumarate, 2 mM $K_4Fe(CN)_6$, 0.1 M 2-(N-morpholino)ethylsulfonic acid (Mes) buffer, having a pH of 6.0. Several reaction mixtures were prepared by dissolving a fixed amount of dopamine-beta-hydroxylase and varied amounts of substrate in constant volumes of the reaction solution. The rate of oxygenation of the substrate in each reaction mixture was measured spectrophotometrically by observing the absorption spectrum of the $Fe(CN)_6^{4-}$ at 420 nm at 37° C. The catalytic constants $k_{cat}$ for each substrate were determined using the procedure of Eisenthal and Cornish-Bowden, Biochem J. 1974, 139, 715–720, or that of Cleland, Adv. Enzymol. Relat. Areas Mol. Biol. 1967, 29, 1–32. The Michaelis-Menten constants for each enzyme-substrate combination were also determined. Three substrates were investigated, 2-phenethylamine(standard), 3-phenylethylamine (analog), 2-aminoethyl phenyl sulfide (compound of the invention). The $k_{cat}$ and ratio of $k_{cat}/K_m$ for each substrate are tabulated in Table I below.

EXAMPLE 2

A reaction solution was prepared having concentrations of 5 micromolar $CuSO_4$, 10 mM sodium fumarate, 10 mM ascorbic acid, 200 microgram/mL catalase, and 0.1 M acetate buffer, having a pH of 5.0. Several reaction mixtures were prepared by dissolving a fixed amount of dopamine-beta-hydroxylase and varied amounts of substrate in constant volumes of the reaction solution. The rate of oxygenation of the substrate was determined by measuring $O_2$ uptake at 37° C. with a Clark polarographic electrode and a YSI Model 53 $O_2$ monitor. The catalytic constant $K_{cat}$ and $K_m$ for each substrate were determined by the same procedure as in Example 1. The same three substrates were investigated as in Example 1, and the results are tabulated in Table 1 below. The reaction for 2-aminoethyl phenyl sulfide may be symbolized by the following equation:

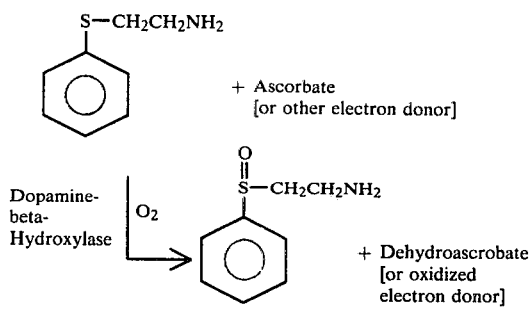

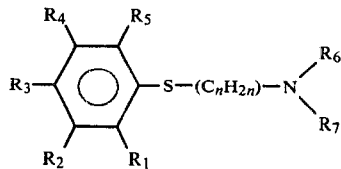

It may be seen from an inspection of the data in Table I that the compound of this invention, 2-aminoethyl phenyl sulfide, is oxygenated at a rate which is much faster than the carbon analog 3-phenylpropylamine. Thus this assay provides a method for evaluating the relative rates of oxygenation of the various aminoalkyl phenyl sulfides which may be used in judging their potential for in vivo activity, in particular anti-hypertensive activity.

TABLE I

| Oxygenated substrate | Electron Donor | | | |
|---|---|---|---|---|
| | $Fe(CN)_6^{4-}$ | | Ascorbic acid | |
| | $k_{cat},s^{-1}$ | $k_{cat}/K_m, M^{-1}s^{-1}$ | $k_{cat},s^{-1}$ | $k_{cat}/K_m, M^{-1}s^{-1}$ |
| 2-phenyl-ethylamine | 19 | $1.9 \times 10^4$ | 65 | $1.9 \times 10^4$ |
| 3-phenyl-propylamine | 1 | $2.0 \times 10^3$ | 12 | $1.0 \times 10^3$ |
| 2-aminoethyl phenyl sulfide | 6 | $4.0 \times 10^3$ | 68 | $3.0 \times 10^3$ |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for treating hypertension in mammals comprising administering to said mammal an effective amount of an aminoalkyl phenyl sulfide having the formula:

$$\text{structure with } R_1, R_2, R_3, R_4, R_5 \text{ on phenyl ring, } S-(C_nH_{2n})-N(R_6)(R_7)$$

wherein
($C_nH_{2n}$) = a linear or branched alkyl chain of 10 carbons or less (n=1-10);
$R_1, R_2, R_3, R_4, R_5$ = H, OH, $C_1$-$C_4$ alkyl, $C_1$-$C_4$-alkoxy, F, Cl, Br, or I;
$R_6, R_7$ = H, $C_1$-$C_4$-alkyl;
or a pharmaceutically acceptable salt thereof.

2. The method of claim 1 wherein $R_1, R_2, R_3, R_4$, and $R_5$ are selected from the group consisting of H, OH, $C_1$-$C_4$-alkyl, and $C_1$-$C_4$-alkoxy.

3. The method of claim 1 wherein $R_1, R_2, R_3, R_4$, and $R_5$ are hydrogen.

4. The method of claim 1 wherein $R_6$ and $R_7$ are hydrogen.

5. The method of claim 1 wherein said aminoalkyl phenyl sulfide is 2-aminoethyl phenyl sulfide.

6. The method of claim 1 wherein said effective amount is 0.5 to 100 mg/kg of body weight of said mammal.

7. The method of claim 1 wherein said effective amount is 1.0 to 10 mg/kg of body weight of said mammal.

8. A pharmaceutical composition comprising a compound of the formula as in claim 1, in an amount effective for treatment of hypertension in mammals, a clinically utilized monoamine oxidase inhibitor, and a pharmaceutically acceptable non-toxic excipient, said monoamine oxidase inhibitor being selected from the group of clinically utilized monoamine oxidase inhibitors consisting of clorgyline, deprenyl, and nardil.

* * * * *